United States Patent
Shibata et al.

[11] Patent Number: 6,160,005
[45] Date of Patent: Dec. 12, 2000

[54] MEDICAMENT FOR CIRCADIAN RHYTHM SLEEP DISORDER

[75] Inventors: Shigenobu Shibata, Tokyo; Takahiro Moriya, Saitama; Michikazu Abe, Kanagawa, all of Japan

[73] Assignee: Mitsubishi Chemical Corporation, Tokyo, Japan

[21] Appl. No.: 09/080,931

[22] Filed: May 19, 1998

[30] Foreign Application Priority Data

May 20, 1997 [JP] Japan ................................. 9-129161

[51] Int. Cl.⁷ .................................................. A61K 31/335
[52] U.S. Cl. ................. 514/452; 514/452; 514/450; 514/418; 514/417; 514/416; 514/415; 514/159; 514/302.4; 549/350; 549/366
[58] Field of Search ..................... 514/159, 418, 514/452, 450, 415, 416, 417, 302.4; 549/350, 366

[56] References Cited

U.S. PATENT DOCUMENTS

| | | | |
|---|---|---|---|
| 4,684,739 | 8/1987 | Kikumoto et al. | 549/350 |
| 5,168,099 | 12/1992 | Iwata et al. | 514/452 |
| 5,234,948 | 8/1993 | Iwata et al. | 514/452 |
| 5,691,325 | 11/1997 | Sandyk | 514/159 |
| 5,776,969 | 7/1998 | James | 514/418 |

FOREIGN PATENT DOCUMENTS 0054304  6/1982  European Pat. Off. .
0446921  9/1991  European Pat. Off. .

OTHER PUBLICATIONS

Bobrzynska et al., Serotonergic Stimulation . . . , Phsyiology and Behavior, v.1, 221–230, 1996.

K. J. Bobrzynska et al.; "Serotonergic Stimulation and Nonphotic Phase–Shifting in Hamsters"; Physiol. Behav., vol. 59, No. 2, 1996, pp. 221–230.

*Primary Examiner*—Jyothsan Venkat
*Assistant Examiner*—Grace Hsu
*Attorney, Agent, or Firm*—Greenblum & Bernstein, P.L.C.

[57] ABSTRACT

A preventive and/or therapeutic medicament for circadian rhythm sleep disorders such as jet lag syndrome which comprises as an active ingredient an alkylenedioxybenzene derivative represented by the following formula (I) wherein m represent an integer of from 2 to 5, and n represents an integer of from 1 to 3, such as 5-[3-[(2S)-(1,4-benzodioxan-2-yl-methyl)amino]propoxy]-1,3-benzodioxol, or a pharmaceutically acceptable salt thereof.

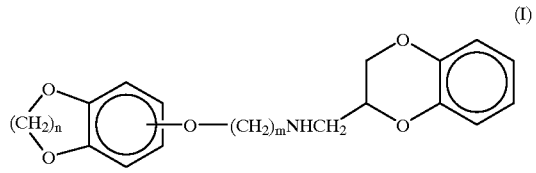

16 Claims, 3 Drawing Sheets

MEDICAMENT FOR CIRCADIAN RHYTHM SLEEP DISORDER

BACKGROUND OF THE INVENTION

1. Field of the Invention

The present invention relates to a medicament useful for preventive and/or therapeutic treatment of sleep disorder. More specifically, the present invention relates to a medicament which comprises a class of alkylenedioxybenzene derivative as an active ingredient, and is useful for preventive and/or therapeutic treatment of circadian rhythm sleep disorders including jet lag syndrome, shift-work sleep disorder, and delayed sleep phase syndrome.

2. Related Art

Circadian rhythm sleep disorder is a disease with patient's present complaint or cardinal symptom of lacking normal sleep in the night, and this disease may sometimes disturb the patient's ordinary social life. This disease includes variety of pathologic states, for example, endogenous chronic syndromes such as delayed sleep syndrome caused by a disruption of the biological clock and its synchronizing mechanism, as well as exogenous acute syndromes such as the symptoms of jet lag and shift-work sleep disorder. Although various drug therapies have been tried for the treatment of circadian rhythm sleep disorders, it has been revealed that only insufficient therapeutic effect can be obtained by hypnotics, including a class of benzodiazepine as a typical example (as a review of pathologic states, therapy or other of circadian rhythm sleep disorders, see, for example, S. Ozaki and K. Okawa, "Sleep Disorder and Biological Rhythm", Special feature: Chronopharmacology, New Guideline of Administration, Molecular Medicine, Vol.34(3), pp.355–365, 1997).

Various factors for synchronization of the biological clock are known. Among them, light is known as a factor having the highest phase-regulating effect. It is also reported that bright light therapy is effective as a therapeutic treatment of circadian rhythm sleep disorders. Accordingly, it is expected that a compound enhancing the photic entrainment of circadian activity rhythm is useful as a therapeutic agent for circadian rhythm sleep disorder. For example, it is known that vitamin B12 is effective for the treatment of sleep phase-delay shift syndrome or other (Takahashi et al., Evolution of circadian clock, pp. 369–382, 1994, Hokkaido University Press), and reported to enhance a light induced phase advance of behavioral circadian rhythm in rats (Ikeda et al., Experimentia, 52, pp.691–694, 1996).

Alkylenedioxybenzene derivatives represented by the following formula are known,

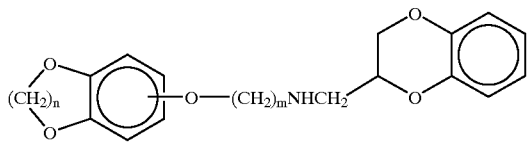

wherein m represents an integer of from 2 to 5, and n represents an integer of from 1 to 3 (Japanese Patent Unexamined Publication (KOKAI) Nos. (Hei)3-264528/1991 and (Hei)4-288072/1992). The publications disclose that the alkylenedioxybenzene derivatives represented by the above general formula bind to a serotonin 1A receptor subtype and exhibit anti-conflict activity, and that they are useful for the treatment of anxiety disorder, schizophrenia, bipolar depression and other.

More specifically, the publications disclose affinity for a serotonin 1A receptor subtype (Ki value) of a m-substituted compound wherein m=3 and n=2 (No. 1), m-substituted compound wherein m=3 and n=2 (No. 2); m-substituted compound wherein m=3 and n=3 (No. 3); m-substituted compound wherein m=4 and n=1 (No. 4), m-substituted compound wherein m=4 and n=3 (No. 6), m-substituted compound wherein m=5 and n=1 (No. 7); and o-substituted compound wherein m=3 and n=1 (No. 13). Furthermore, publications also disclose that Compound No. 1, Compound No. 2, and Compound No. 3 mentioned above have anti-conflict activity, and are useful for the treatment of anxiety disorder, schizophrenia, bipolar depression and other. However, these publications neither teach nor suggest an effectiveness of the aforementioned compounds for therapeutic treatment of circadian rhythm sleep disorders.

The object of the present invention is to provide a medicament useful for preventive and/or therapeutic treatment of sleep disorders. More specifically, the object is to provide a medicament capable of effectively preventing and/or treating circadian rhythm sleep disorders such as delayed sleep phase syndrome, non-24-hour sleep-wake disorder, jet lag syndrome, and shift work sleep disorder.

SUMMARY OF THE INVENTION

The present inventors conducted various studies to achieve the foregoing object, and as a result, they found that a certain class of alkylenedioxybenzene derivatives remarkably enhance a photo-induced phase-regulation effect on a circadian rhythm and synchronize a living body with the biological clock. The present invention was achieved on the basis of these findings.

The present invention thus provides preventive and/or therapeutic medicament for sleep disorders, preferably circadian rhythm sleep disorders, which comprises as an active ingredient an alkylenedioxybenzene derivative represented by the following formula (I);

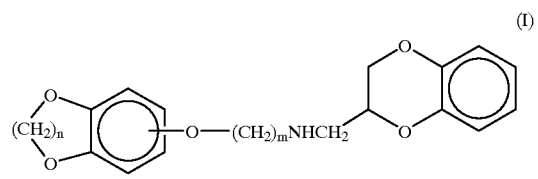

wherein m represent an integer of from 2 to 5, and n represents an integer of from 1 to 3 or a pharmaceutically acceptable salt thereof, or a hydrate thereof or a solvate thereof.

As preferred embodiments of the present invention, there are provided the aforementioned preventive and/or therapeutic medicament wherein the circadian rhythm sleep disorder is jet lag syndrome, shift-work sleep disorder, or delayed sleep phase syndrome; the aforementioned preventive and/or therapeutic medicament which is used for prevention and/or therapeutic treatment of various symptoms resulting from senile circadian rhythm sleep disorder, e.g., delirium and nocturnal dromomania, caused by an abnormal circadian rhythm due to aging; and the aforementioned preventive and/or therapeutic medicament which is used for bright light therapy. As a further preferred embodiment of the present invention, there is provided the aforementioned preventive and/or therapeutic medicament which comprises a compound according to the above formula (I) wherein n is 1, and most preferably 5-[3-[(2S)-(1,4-benzodioxan-2-yl-methyl)amino]propoxy]-1,3-benzodioxol or a physiologically acceptable salt thereof, or a hydrate thereof or a solvate thereof.

According to another preferred embodiment of the present invention, the aforementioned preventive and/or therapeutic medicament is provided in the form of a pharmaceutical composition comprising an alkylenedioxybenzene derivative represented by the above formula (I) and one or more pharmaceutical additives. According to further aspect of the present invention, there are provided use of a substance selected from the group consisting of the alkylenedioxybenzene derivatives represented by the above formula (I) and physiologically acceptable salts thereof, and hydrates thereof and solvates thereof, for the manufacture of the aforementioned preventive and/or therapeutic medicament; and a method for preventive and/or therapeutic treatment of a circadian rhythm sleep disorder which comprises the step of administering to a mammal including human a preventively and/or therapeutically effective amount of a substance selected from the group consisting of the alkylenedioxybenzene derivatives represented by the above general formula (I) and physiologically acceptable salts thereof, and hydrates thereof and solvates thereof.

DETAILED EXPLANATION OF THE INVENTION

Figure 1:
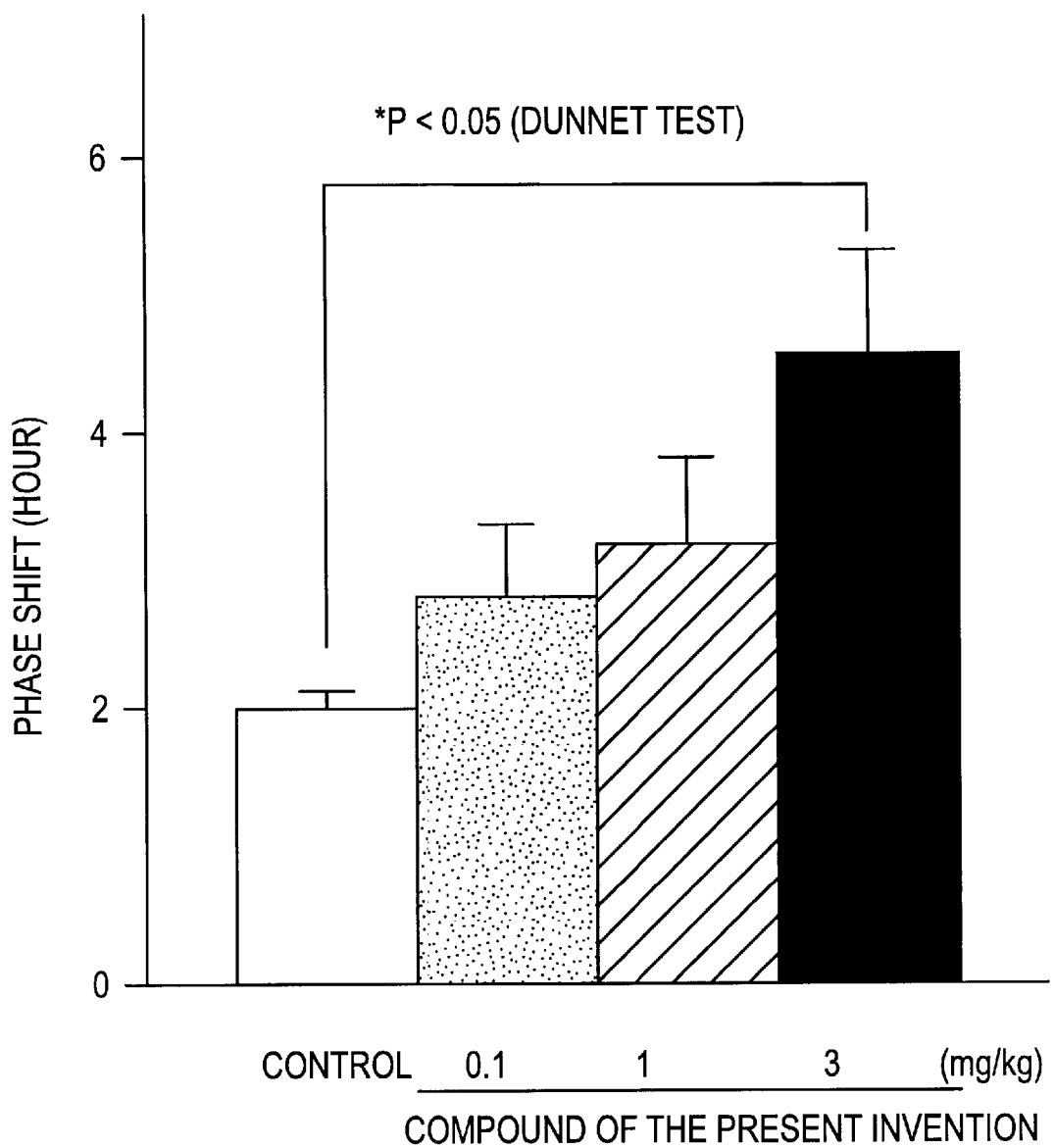
FIG. 1 shows the effect of the medicament of the present invention (administered 30 minutes before light pulse) on light pulse-induced phase advance of wheel-running rhythm in hamsters.

The preventive and/or therapeutic medicament of the present invention is characterized in that it comprises the alkylenedioxybenzene derivative represented by the formula (I) or a pharmaceutically acceptable salt thereof, or a hydrate thereof or a solvate thereof as an active ingredient. The alkylenedioxybenzene derivatives represented by the general formula (I) are known and described in, for example, Japanese Patent Unexamined Publication (KOKAI) Nos. (Sho)57-108088/1982, (Sho)58-219114/1983 and (Hei) 3-264528/1991, and accordingly, they are readily obtainable by those skilled in the art. Among the alkylenedioxybenzene derivatives of the above formula (I), those wherein n is 1 are preferred. The aminoalkyleneoxy group binding to the phenyl group may be at either ortho-position or meta-position relative to one of the oxygen atoms of the alkylenedioxy group. The meta-position is more preferred.

As the active ingredient of the medicament of the present invention, the alkylenedioxybenzene derivatives of the general formula (I) in the free form may be used, and in addition, physiologically acceptable salts thereof may also be used. Examples of the salts include, for example, mineral acid salts such as hydrochlorides, phosphates and sulfates; and organic acid salts such as acetates, formates, citrates and p-toluenesulfonates. Furthermore, any hydrates or solvates of the compounds in the free form or the salts may also be used as the active ingredient of the medicament of the present invention. Solvents that may form the solvates are not particularly limited so long as they are physiologically acceptable. Examples of the solvent include methanol, ethanol, isopropanol, acetone and ethyl acetate. Among them, ethanol solvates or other may preferably be used.

The alkylenedioxybenzene derivative represented by the formula (I) has one asymmetric carbon, and two enantiomers exist resulted therefrom. A method for preparation of the enantiomers and their pharmaceutical use are described in Japanese Patent Unexamined Publication (KOKAI) No. (Hei) 4-288072/1992, and both of the enantiomers are available to those skilled in the art. As the active ingredients of the medicament of the present invention, optically pure enantiomers of the aforementioned alkylenedioxybenzene derivatives or any mixture of the enantiomers may be used. When optically pure enantiomers are used, those in S-configuration are preferred. Furthermore, a racemate, which is an equimolar mixture of two enantiomers, may also be used.

Examples of the alkylenedioxybenzene derivatives preferred as the active ingredient of the medicament of the present invention are shown below. However, the active ingredients if the medicament of the present invention are not limited to the following compounds.

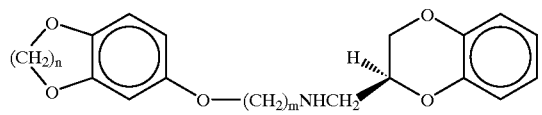

TABLE 1

| Compound No. | m | n |
|---|---|---|
| 1 | 3 | 1 |
| 2 | 3 | 2 |
| 3 | 3 | 3 |
| 4 | 4 | 1 |
| 5 | 4 | 2 |
| 6 | 4 | 3 |
| 7 | 5 | 1 |
| 8 | 5 | 2 |
| 9 | 5 | 3 |
| 10 | 2 | 1 |
| 11 | 2 | 2 |
| 12 | 2 | 3 |

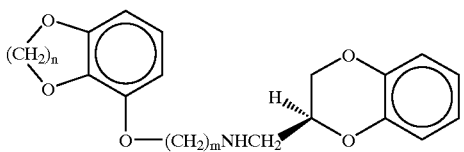

TABLE 2

| Compound No. | m | n |
|---|---|---|
| 13 | 3 | 1 |
| 14 | 3 | 2 |
| 15 | 3 | 3 |
| 16 | 4 | 1 |
| 17 | 4 | 2 |
| 18 | 4 | 3 |
| 19 | 5 | 1 |
| 20 | 5 | 2 |
| 21 | 5 | 3 |
| 22 | 2 | 1 |

TABLE 2-continued

| Compound No. | m | n |
|---|---|---|
| 23 | 2 | 2 |
| 24 | 2 | 3 |

Among the compounds listed in Tables 1 and 2 shown above, Compound No. 1 is particularly preferred. This compound is specifically described in Japanese Patent Unexamined Publication (KOKAI) Nos. (Hei) 3-264528/1991 and (Hei) 4-288072/1992. These publications disclose that the alkylenedioxybenzene derivatives of formula (I), the active ingredient according to the present invention, have high affinity for a serotonin 1A receptor subtype and anti-conflict activity. In addition, those publications also disclose that the alkylenedioxybenzene derivatives are useful for therapeutic treatment of anxiety disorder, schizophrenia, bipolar depression and other diseases. However, the publications neither suggest nor teach that these derivatives are useful for the treatment of circadian rhythm sleep disorders.

Although if id not intended to be bound to any specific theory, the medicament of the present invention remarkably enhances the light-induced phase advance of circadian activity rhythm under constant dark condition, and also remarkably enhances the photic entrainment of circadian activity rhythm. Therefore, the medicament of the present invention is useful for preventive and/or therapeutic treatment of endogenous circadian rhythm sleep disorders such as delayed sleep phase syndrome and senile circadian rhythm sleep disorder, and the medicament is also useful for preventive and/or therapeutic treatment of symptoms resulted from sleep disorder caused by an abnormal circadian rhythm due to aging such as delirium and nocturnal dromomania.

Furthermore, the medicament of the present invention is also useful for preventive and/or therapeutic treatment of exogenous circadian rhythm sleep disorders caused by environmental alteration such as jet lag syndrome or shift-work sleep disorder. The medicament of the present invention may be used in combination with one or more other drug therapies for the purpose of preventive and/or therapeutic treatment of circadian rhythm sleep disorders, and the medicament may also be used as an auxiliary drug to enhance therapeutic effects of a physiotherapy such as bright light therapy.

A substance selected from the group consisting of the aforementioned alkylenedioxybenzene derivatives and their pharmaceutically acceptable salts, and hydrates thereof and solvates thereof may be administered, per se, to a mammal including human. Generally, however, it is preferred to prepare a pharmaceutical composition comprising at least one of the above substances as an active ingredient and one or more pharmaceutical additives, and administer the composition to a patient. Examples of such a pharmaceutical composition includes, for example, pharmaceutical preparations for oral administration such as tablets, capsules, granules, powders, pills, troches, sublingual tablets and liquids, and pharmaceutical preparations for parenteral administration such as injections, drip infusions, suppositories, transdermal preparations, transmucosal preparations, inhalants, and patches for transdermal absorption.

Tablets and capsules for oral administration are usually provided in a unit dosage form, and they may be prepared by using one or more ordinary pharmaceutical additives such as binders, fillers, diluents, compressing agents, lubricants, disintegrators, colorants, flavoring agents, and moistening agents. Tablets may be coated by using, for example, an enteric coating agent according to a method well-known in the art, and they may be prepared by using fillers such as cellulose, mannitol and lactose; disintegrators such as starch, polyvinylpyrrolidone, starch derivatives and sodium starch glycolate; lubricants such as magnesium stearate; and moistening agents such as sodium laurylsulfate.

Liquid preparations for oral administration can be provided as, for example, aqueous or oil suspensions, solutions, emulsions, syrups, and elixirs. They may also be provided as dried pharmaceutical preparations such as lyophilized preparations which can be dissolved by adding water or suitable aqueous medium before use. These liquid medicaments may be formulated with ordinary pharmaceutical additives such as, for example, suspending agents such as sorbitol, syrups, methylcellulose, gelatin, hydroxyethylcellulose, carboxymethylcellulose, aluminum stearate gel and hydrogenated edible fat; emulsifiers such as lecithin, sorbitan monooleate and gum arabic; non-aqueous mediums such as almond oil, rectified coconut oil, oily esters (e.g., glycerin esters), propylene glycol, ethyl alcohol (including edible oils); preservatives such as methyl ester, ethyl ester and propyl ester of p-hydroxybenzoic acid and sorbic acid; and ordinary flavoring agents and colorants, as required.

The pharmaceutical preparations for oral administration can be produced by methods well known in the art such as mixing, filling, and compressing. By repeated combined procedures, the active ingredient can be distributed in a pharmaceutical preparation composed of a large amount of filler and other. The pharmaceutical preparations for parenteral administration such as injections and drip infusions are generally provided as unit dosage pharmaceutical preparations containing the aforementioned substances as the active ingredient and a sterilized medium, and the preparations can be prepared by dissolving the aforementioned substances in a suitable medium and subjecting the resulting solution to sterilization filtration, and then filling the solution in suitable vials or ampoules, followed by sealing the containers. To enhance stability, the composition may be frozen and filled in vials, and then moisture may be removed under reduced pressure. Suspensions for parenteral administration can be prepared substantially in the same manner as the solutions for parenteral administration, and they can preferably be prepared by suspending the active ingredient in a medium and sterilizing the suspension by means of a gas such as ethylene oxide. To obtain uniform distribution of the active ingredient, surfactants or moistening agents may be added as required.

The dose of the medicament of the present invention may be suitably chosen in view of, for example, therapeutic or preventive purpose, a kind of a disease to be treated or prevented, and symptom, body weight, age, sexuality or other of a patient. For oral administration for an adult, the medicament can generally be administered in an amount of about 0.01 mg to 1,000 mg, preferably 1 to 100 mg per day as an amount of the active ingredient. The daily dose may be administered once a day, or several times a day as divided portions.

EXAMPLE

The present invention will be explained more specifically by referring to the following example. However, the scope of the present invention is not limited to the example. In the example, Compound No. 1 (m=3, n=1, meta-substituted compound: hereinafter referred to as "medicament of the present invention") exemplified in the above Table 1 was used as an active ingredient of the medicament of the present invention.

Example 1

Hamsters were raised under constantly dark condition in a breeding cage provided with a running wheel. Activity rhythms of the hamsters were judged every day based on rotation number of the running wheel. The hamsters raised under constant dark condition exhibited an activity rhythm of an approximately 24-hour cycle (a circadian rhythm). The onset of the active phase was considered as circadian time (CT) 12. After 2-week breeding, the animals were exposed to light pulse (60 lux for 15 minutes) at CT 20. Thirty minutes before the light and 5 or 60 minutes after the light, the medicament of the present invention was intraperitoneally administered to the animals. The light pulse, per se, advanced the circadian rhythm by approximately two hours (FIG. 1). When the medicament of the present invention was administered 30 minutes before the light pulse, the phase-advancing effect was enhanced dose-dependently, and a significant difference was observed at a dose of 3 mg/kg (FIG. 1).

Figure 2:
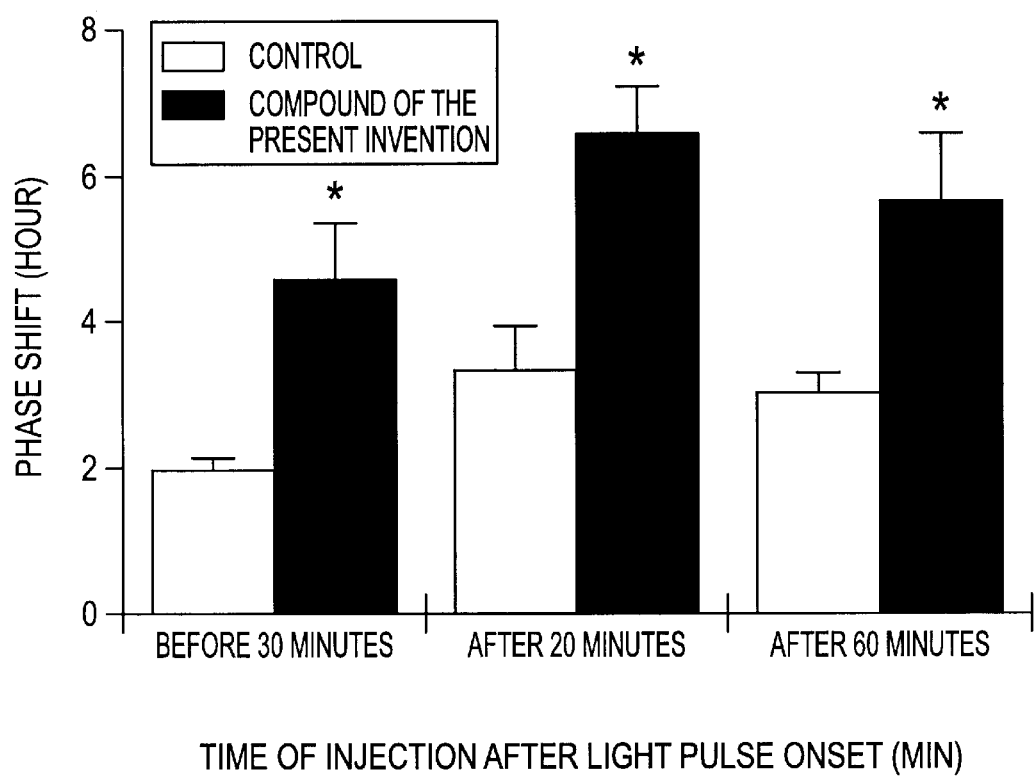
FIG. 2 shows the effect of the medicament of the present invention, administered at different timings, on the light pulse-induced phase advance of wheel-running rhythm in hamsters. In the figure, * indicates a significant difference compared to a control group with significance level of 5%.
Figure 3:
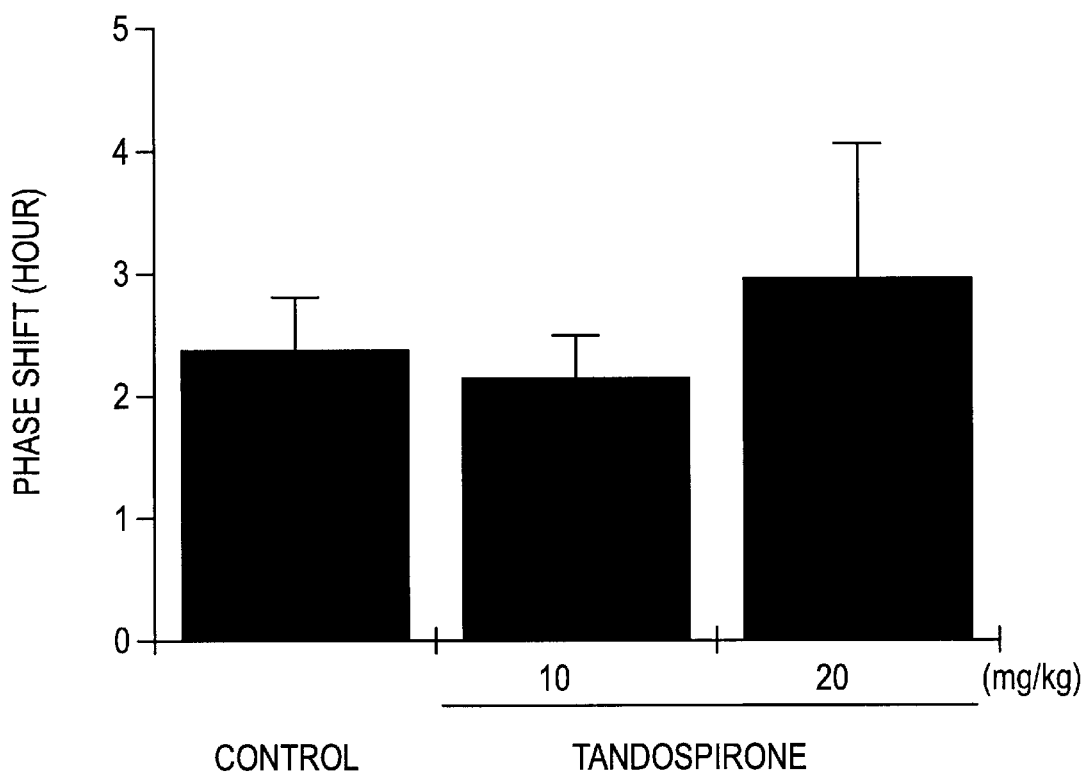
FIG. 3 shows the effect of tandospirone (a reference compound), administered 30 minutes before the light pulse, on the light-pulse-induced phase advance of wheel-running rhythm in hamsters.

When the medicament of the present invention was administered 5 minutes or 60 minutes after the light pulse, the enhancement of the light-induced phase advance was also observed (FIG. 2). However, the compound, per se, has no effect on the circadian rhythm without light. On the other hand, tandospirone, a partial agonist of serotonin 1A receptors administered at a dose of 10 and 20 mg/kg, exhibited no significant difference of the light-induced phase advance (FIG. 3). These results suggest that the enhancing effect of the medicament of the present invention on light synchronization was not solely resulted from a stimulation of the serotonin 1A receptor.

The medicament of the present invention enhances the phase-shift of a circadian activity rhythm induced by light, and therefore, the medicament is useful for preventive and/or therapeutic treatment of sleep disorders such as circadian rhythm sleep disorders.

What is claimed is (for U.S.):

1. A method for therapeutic treatment of a sleep disorder which comprises administering to a mammal in need of such treatment, a therapeutically effective amount of a substance selected from the group consisting of an alkylenedioxybenzene derivative represented by the following formula (I):

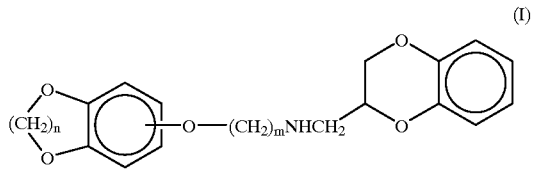

(I)

wherein m represents an integer of from 2 to 5, and n represents an integer of from 1 to 3, and a pharmaceutically acceptable salt thereof, a hydrate thereof, and a solvate thereof.

2. The method according to claim 1, wherein the sleep disorder is a circadian rhythm sleep disorder.

3. The method according to claim 1, wherein the alkylenedioxybenzene derivative is 5-[3-[(2S)-(1,4-benzodioxan-2-yl-methyl)amino]propoxy]-1,3-benzodioxol.

4. The method according to claim 2, wherein the circadian rhythm sleep disorder is jet lag syndrome.

5. The method according to claim 2, wherein the circadian rhythm sleep disorder is shift-work sleep disorder.

6. The method according to claim 2, wherein the circadian rhythm sleep disorder is delayed sleep phase syndrome.

7. The method according to claim 1, which is carried out for therapeutic treatment of symptoms resulted from a senile circadian rhythm sleep disorder.

8. The method according to claim 1, which is carried out together with bright light therapy.

9. A method for therapeutic treatment of a sleep disorder which comprises administering to a mammal in need of such treatment, a therapeutically effective amount of medicament consisting essentially of a member selected from the group consisting of an alkylenedioxybenzene derivative represented by the following formula (I):

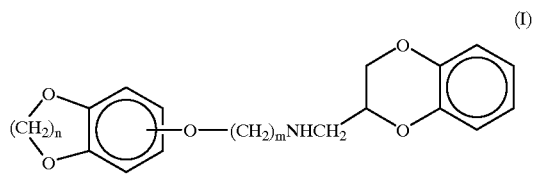

(I)

wherein m represents an integer of from 2 to 5, and n represents an integer of from 1 to 3, and a pharmaceutically acceptable salt thereof, a hydrate thereof, and a solvate thereof.

10. The method according to claim 9, wherein the sleep disorder is a circadian rhythm sleep disorder.

11. The method according to claim 9, wherein the alkylenedioxybenzene derivative is 5-[3-[(2S)-(1,4-benzodioxan-2-yl-methyl)amino]propoxy]-1,3-benzodioxol.

12. The method according to claim 10, wherein the circadian rhythm sleep disorder is jet lag syndrome.

13. The method according to claim 10, wherein the circadian rhythm sleep disorder is shift-work sleep disorder.

14. The method according to claim 10, wherein the circadian rhythm sleep disorder is delayed sleep phase syndrome.

15. The method according to claim 9, which is carried out for therapeutic treatment of symptoms resulted from a senile circadian rhythm sleep disorder.

16. The method according to claim 9, which is carried out together with bright light therapy.

* * * * *